(12) United States Patent
Gillet et al.

(10) Patent No.: US 10,047,195 B2
(45) Date of Patent: Aug. 14, 2018

(54) MONOMERS BEARING ASSOCIATIVE GROUPS FOR THE SYNTHESIS OF SUPRAMOLECULAR POLYCONDENSATES

(71) Applicant: Arkema France, Colombes (FR)

(72) Inventors: Jean-Philippe Gillet, Brignais (FR); Jean-Pierre Disson, Vernaison (FR); Bruno Van Hemelryck, Chaponost (FR)

(73) Assignee: Arkema France, Colombes (FR)

( * ) Notice: Subject to any disclaimer, the term of this patent is extended or adjusted under 35 U.S.C. 154(b) by 217 days.

(21) Appl. No.: 14/389,923

(22) PCT Filed: Mar. 28, 2013

(86) PCT No.: PCT/FR2013/050682
§ 371 (c)(1),
(2) Date: Oct. 1, 2014

(87) PCT Pub. No.: WO2013/150221
PCT Pub. Date: Oct. 10, 2013

(65) Prior Publication Data
US 2015/0065679 A1 Mar. 5, 2015

(30) Foreign Application Priority Data
Apr. 2, 2012 (FR) ..................................... 12 52993

(51) Int. Cl.
*C08G 63/685* (2006.01)
*C08G 83/00* (2006.01)
*C07D 233/36* (2006.01)

(52) U.S. Cl.
CPC ....... *C08G 63/6856* (2013.01); *C07D 233/36* (2013.01); *C08G 83/008* (2013.01)

(58) Field of Classification Search
None
See application file for complete search history.

(56) References Cited

U.S. PATENT DOCUMENTS

| 2,858,319 | A | | 10/1958 | Benneville |
| 5,496,907 | A | * | 3/1996 | Dochniak ............ C07D 233/32 252/182.18 |
| 8,076,398 | B2 | | 12/2011 | Gonzalez Leon |
| 2011/0183098 | A1 | | 7/2011 | Hidalgo |

FOREIGN PATENT DOCUMENTS

| DE | 3214909 | 10/1983 |
| WO | 9420474 | 9/1994 |
| WO | 9607644 | 3/1996 |
| WO | 2009054904 | 4/2009 |
| WO | 2010031956 | 3/2010 |
| WO | 2011015773 | 2/2011 |

OTHER PUBLICATIONS

International Search Report for International Application No. PCT/FR2013/050682 dated Aug. 29, 2013.
Written Opinion of the International Searching Authority for International Application No. PCT/FR2013/050682 dated Aug. 29, 2013.

* cited by examiner

*Primary Examiner* — Ling Siu Choi
*Assistant Examiner* — Thuy-Ai N Nguyen
(74) *Attorney, Agent, or Firm* — RatnerPrestia

(57) ABSTRACT

The present invention relates to the use of monomers bearing associative groups in order to manufacture a supramolecular polycondensate, to certain of these monomers, to a process for manufacturing a supramolecular polycondensate, to the polycondensate obtained, and also to an article or a composition incorporating same. The associative groups may be, for example, imidazolidone, urea or triazole groups.

20 Claims, No Drawings

MONOMERS BEARING ASSOCIATIVE GROUPS FOR THE SYNTHESIS OF SUPRAMOLECULAR POLYCONDENSATES

CROSS-REFERENCE TO RELATED APPLICATIONS

This application is a U.S. National Phase Application of International Application No. PCT/FR2013/050682, filed Mar. 28, 2013, which claims priority to French Patent Application No. 1252993, filed Apr. 4, 2012. The entire contents of both applications are incorporated by reference herewith for all purposes.

FIELD OF THE INVENTION

The present invention relates to the use of monomers carrying associative groups to manufacture a supramolecular polycondensate, to some of these monomers, to a process for the manufacture of a supramolecular polycondensate, to the polycondensate obtained and to an article or a composition incorporating it.

DISCUSSION OF THE RELATED ART

"Supramolecular" polymers are materials carrying associative groups, that is to say groups capable of forming one or more noncovalent bonds, in particular hydrogen bonds. One advantage lies in the fact that these bonds, of physical nature, are reversible, in particular under the influence of the temperature or by the action of a selective solvent.

The manufacture of supramolecular polymers remains to this day a complex operation. It is generally necessary to start from a preformed polymer, to which "associative" molecules will be grafted, which molecules confer, on the polymer, a supramolecular nature. This behavior is displayed in particular by a strengthening of the cohesion of the network of the polymer, due to the formation of a physical network (reversible physical bonds) in addition to its existing chemical network (covalent bonds).

Mention may be made, as illustration of supramolecular polymers obtained by the route of modifying an existing polymer, of the document WO 2010/031956 of the applicant company, which describes elastomers comprising flexible polymer chains associative with one another, on the one hand, via crosslinking bridges having covalent bonds and, on the other hand, via crosslinking bridges having noncovalent bonds. In contrast to conventional elastomers, these supramolecular elastomers have the advantage of being able to fluidize above a certain temperature, which facilitates the processing thereof, in particular the satisfactory filling of molds, and also the recycling thereof. The process for the manufacture of these supramolecular elastomers comprises a stage of functionalization of an elastomer and then a stage of grafting molecules comprising, on the one hand, an associative group and, on the other hand, a reactive group which forms a covalent bond with a reactive functional group carried by the elastomer.

Another method of preparation mentioned in the prior art consists in introducing associative monomers at chain ends of a polymer, that is to say as chain terminators of a polymer. This makes it possible in particular to prepare supramolecular polycondensation polymers (or polycondensates) of polyimide or polyurethane type. However, this method of preparation does not make it possible to introduce associative molecules other than at chain ends.

For other polycondensation polymers, such as the polyesters, it is possible to graft associative molecules within the chain (meaning the other points of the chain than at its ends), provided that the chain is functionalized beforehand in order to create grafting sites, for example by maleinization. However, this process remains complex from the view point of the synthesis of the polymer, proves to be expensive and exerts a random grafting yield.

The applicant company has also described, in the past, supramolecular polymers obtained by polycondensation employing compounds carrying associative groups. Mention may be made, on this account, of the document WO 2011/015773, which describes a bituminous composition comprising an asphalt and a supramolecular polycondensate. In the examples, the polycondensates synthesized are obtained from monofunctional associative molecules, namely comprising, on the one hand, an associative group and, on the other hand, a reactive group, with the result that the polycondensates formed carry associative groups only at their chain ends.

Nevertheless, there exist applications where the polycondensate is stressed mechanically or thermally and it is essential to be able to increase the amount of associative groups per polymer chain and/or to be able to adjust their position on the chain in order to maximize the performance, in particular mechanical and/or thermal, of the polycondensate.

Thus, the materials and/or the manufacturing processes of the state of the art are not entirely satisfactory.

There still exists a need to have available polycondensates with improved properties, having in particular a stronger polymer network cohesion than that of the polycondensates of the state of the art and/or demonstrating a better temperature behavior or a better mechanical strength than the latter.

There exists in particular a need to have available supramolecular polycondensates, the number of associative groups of which incorporated per polymer chain and/or their position in the chain can be controlled with precision and/or be adjusted at will. There very particularly exists a need for polycondensates carrying pendant associative groups (that is to say, other than at chain ends), distributed within the chain, and in controlled fashion.

Finally, there exists a need for a process for the manufacture of supramolecular polymers which is not very expensive, which can be carried out easily and/or reliably and reproducibly with regard to the result expected, in particular as regards the configuration of the chains of the polymer obtained, and/or which can be adjusted to different natures of polycondensates, very particularly polyamides, polyesters, poly(thioester)s, polyurethanes, polyureas, polyethers, polyimines and polyamines, to mention only the main ones among them.

SUMMARY OF THE INVENTION

The term "at least difunctional monomer" is understood to mean a monomer carrying at least two reactive functional groups capable of participating in the growth of a polymer chain and in particular in the formation of the unit of a polycondensate.

Consequently, a first subject matter of the invention is the use, in order to manufacture a polycondensate, of an at least difunctional monomer (A) corresponding to the formula (I):

$$X_1-R_1-X-R_1'-X_1' \quad (I)$$
$$\underset{\underset{B}{|}}{\overset{|}{R_2}}$$

in which:

$X_1$ and $X_1'$, which are referred to as "reactive functional groups", denote identical or different functional groups independently chosen from $-NH_2$, $-COOH$, $-PO_3H$, $-OPO_3H$, $-OH$, $-SH$, $-COSH$, $-CSSH$, $-CSOH$, -halogen, $-CN$, $-NCO$, $-NCS$ or -epoxy, X denotes the nitrogen or phosphorus atom, the $P(=O)O_3$ group, a saturated, partially unsaturated or completely unsaturated $C_4$-$C_7$, preferably $C_5$-$C_6$, hydrocarbon ring which is optionally interrupted by one or more heteroatoms chosen from nitrogen, oxygen, silicon, phosphorus or sulfur; or a $CR_3$, $SiOR_3$, $SiR_3$ or $SiHal$ group where $R_3$ is chosen from the hydrogen atom or a linear or branched $C_1$-$C_{20}$, preferably $C_1$-$C_6$, alkyl radical and Hal represents the F, Cl, Br or I atom and preferably the Cl atom, $R_1$, $R_1'$ and $R_2$, which are identical or different, represent, independently of one another, a single bond or a saturated or unsaturated and linear or branched $C_1$-$C_{30}$, preferably $C_1$-$C_{20}$, indeed even $C_1$-$C_{10}$, hydrocarbon chain which is optionally substituted and optionally interrupted by one or more heteroatoms chosen from nitrogen, oxygen, silicon, phosphorus or sulfur or by a saturated, partially unsaturated or completely unsaturated hydrocarbon ring optionally comprising one or more heteroatoms chosen from nitrogen, oxygen and sulfur, B denotes an associative group chosen from the groups (B1) to (B4):

(B1)

(B2)

(B3)

(B4)

in which:

Z represents an oxygen or sulfur atom or an $-NH$ group, preferably an oxygen atom, R represents a saturated or unsaturated and linear or branched $C_1$-$C_{10}$ alkyl group.

The term "reactive functional groups" is understood to mean chemical functional groups capable of reacting with other chemical functional groups to form, by condensation reaction, covalent bonds, resulting in particular in the formation of repeat units characteristic of polycondensates, such as amide, ester, thioester, urethane, urea, ether, imine and amine units. In one embodiment, the amide, ester, urethane and urea units are preferred.

Reference will be made, in the continuation, to "at least monofunctional" compound to denote a compound carrying at least one reactive functional group.

Reference will be made to "at least difunctional" compound to denote a compound carrying at least two identical or different reactive functional groups.

The term "polycondensate" is understood to mean a polymer or copolymer obtained by polycondensation reaction. Polycondensation is defined by a reaction mechanism resulting in the formation of a polymer or copolymer with general elimination of a small molecule, for example water in the case of the formation of polycondensates of polyamide or polyester type, or without elimination of a small molecule, for example in the case of the formation of polyurethanes or epoxies. Polycondensation is a polymerization, the phase of growth of the molecular chains of which involves reactions between reactive functional groups of at least difunctional monomers.

"Substituted" $C_1$-$C_{30}$ hydrocarbon chain, with regard to $R_1$, $R_1'$ and $R_2$, should be understood as meaning a branched $C_1$-$C_{30}$, preferably $C_1$-$C_{20}$, hydrocarbon chain which is saturated or unsaturated and/or substituted by one or more $=O$, $-OH$, $-NH_2$ or -halogen groups and/or interrupted by one or more heteroatoms, such as $-O-$.

It is understood that $R_1$, $R_1'$ and $R_2$ do not comprise a carbamate $$-N-C(=O)-O-$$
$$|$$

group.

Another subject matter of the invention is a process for the manufacture of a polycondensate by any technique known to a person skilled in the art and employing at least one monomer (A) as defined above.

In a preferred embodiment, the monomer (A) is employed in a content ranging from 0.1 mol % to 100 mol %, preferably from 1 mol % to 80 mol %, indeed even from 1 mol % to 50 mol %, with regard to the total number of moles of monomers used to manufacture the polycondensate.

In another embodiment, the monomer (A) is employed in a content ranging from 0.1 mol % to 100 mol %, preferably from 0.5 mol % to 100 mol %, from 1 mol % to 100 mol %, from 5 mol % to 100 mol %, from 10 mol % to 100 mol %, indeed even from 40 mol % to 100 mol %, with regard to the total number of moles of at least difunctional monomers used to manufacture the polycondensate.

In another embodiment, the monomer (A) is employed in a content ranging from 20 mol % to 95 mol %, from 30 mol % to 70 mol %, indeed even from 40 mol % to 60 mol %, with regard to the total number of moles of at least difunctional monomers used to manufacture the polycondensate.

As will be seen subsequently, the remainder 100% can advantageously be contributed by another monomer (C) other than (A) which is at least monofunctional, advantageously difunctional, and which does not comprise an associative group.

Another subject matter of the invention is the polycondensate carrying pendant associative group(s) capable of being obtained by this manufacturing process.

Some of the monomers (A) are novel and, as such, form another subject matter of the present invention. Thus, the invention also relates to the monomers (A') of abovementioned formula (I) with the restriction that, when X represents the N atom and:

$R_1=R_1'=\!\!=\!\!-CH_2\!\!-\!\!$, then $X_1$ and $X_1'$ cannot simultaneously represent COOH, $X_1=X_1'=\!\!$OH or CN, then $R_1$ and $R_1'$ cannot simultaneously represent —$CH_2$—$CH_2$—.

It should be noted that the document DE 3214909 describes cationic derivatives and their use to improve the attachment of dyes to fabrics. Example 2 discloses the reaction of N-(2-aminoethyl)imidazolidin-2-one with ethylene oxide to form 1-[2-[bis(2-hydroxyethyl)amino]ethyl] imidazolidin-2-one, which is involved as intermediate in the synthesis of a cationic derivative in accordance with the teaching of the document. This intermediate is thus not intended to be employed in polymerization.

For its part, the document U.S. Pat. No. 2,858,319 teaches imidazolidinone derivatives, said to be of use as sequestering agents for polyvalent metal ions, including a diacid carrying an imidazolidinyl group: 1-[β-(N,N-bis(carboxymethyl)amino)ethyl]-2-imidazolidinone. The document neither describes nor suggests that these derivatives are employed in polymerization.

For its part, the document WO 94/20474 teaches diamines based on imidazolidone and their derivatives as chain-extending monomers intended to provide pendant imidazolidinone groups to epoxy or polyurethane/urea polymers. Example 3 of the document discloses the following derivative:

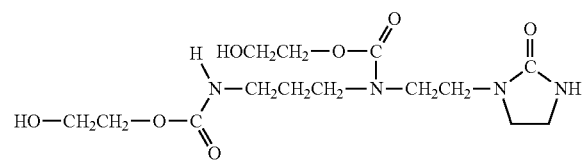

This derivative comprises heat-reversible carbamate N—C (=O)—O bridges. Thus, when the derivative is heated to a temperature in the vicinity of 190° C., it decomposes to give isocyanate and alcohol. Consequently, if such a derivative is employed during a polycondensation carried out within this temperature range and during which water is given off, the isocyanate reacts with the water to form an amine and carbon dioxide gas. The change in functionality and the bubbling which are occasioned do not make it possible to prepare a supramolecular polycondensate in a controlled manner.

Finally, a subject matter of the invention is the use of the polycondensate in accordance with the invention to manufacture a polymer article or a polymer composition, and also the polymer articles and compositions obtained.

The present invention advantageously makes it possible to synthesize polycondensates exhibiting a higher apparent molecular weight under ambient conditions than that of conventional polycondensates not carrying associative groups. It is thus possible to reduce the length of the chains of polycondensates and thus to fluidize the chains under hot conditions without, however, losing mechanical strength of the polycondensate.

In addition, the present invention makes it possible to synthesize supramolecular polycondensates which, in contrast to those known from the state of the art (which exhibit associative groups solely at the chain end), comprise pendant associative groups on the chain, the number and the position of which on the chain can be adjusted and controlled at will. It is thus possible to adapt the structure of the polymer chain as a function of the properties as desired in the final polycondensate, for example by employing one or more of the following means:

order of addition of the monomers, in order to obtain random or block polymers, for example;

(monomer(s) carrying associative group(s)/total sum of the monomers employed) ratio, in order to obtain polymers having a predetermined content of associative groups, for example;

introduction of the monomers as more or less concentrated formulations in a solvent, for controlled management of the polycondensation reaction;

and others.

In addition, in contrast with the majority of the known processes of the state of the art (which consist in grafting associative molecules to existing polymers), the process for the manufacture of the polycondensates according to the invention principally employs a polycondensation, which exhibits the advantage of being a simple chemistry which is easy to implement and control. The process for the manufacture of polycondensates according to the invention in addition exhibits a good yield for incorporation of associative molecules per polymer chain and/or great precision with regard to the number of associative molecules incorporated and/or with regard to their position in the chain.

DETAILED DESCRIPTION

The invention will now be described in more detail and without implied limitation in the following description.

When reference is made to intervals, the expressions of the "ranging from . . . to . . . " type include the limits of the interval, whereas the expressions of the "of between . . . and . . . " type exclude the limits of the interval.

Unless otherwise mentioned, the percentages expressed are percentages by weight.

Unless otherwise mentioned, the parameters to which reference is made are measured at atmospheric pressure and at ambient temperature (20° C.).

Monomer (A)

The monomer (A) exhibits the abovementioned general formula (I). It can, of course, exhibit a more specific formula, according to any one of the advantageous embodiments of the invention stated below, optionally combined with one another.

According to one embodiment of the invention, $X_1$ and $X_1'$ denote reactive functional groups independently chosen from —$NH_2$, —COOH, —OH, —NCO or —CN.

According to a more specific embodiment of the invention, $X_1$ and $X_1'$ denote reactive functional groups independently chosen from —$NH_2$, —COOH or —OH.

According to one embodiment of the invention, $X_1$ and $X_1'$ denote different reactive functional groups, preferably functional groups capable of reacting with one another. This makes it possible, for example, to manufacture a polycondensate by condensation of monomers (A) exclusively.

According to one embodiment of the invention, X denotes a nitrogen or phosphorus atom or a $CR_3$ group where $R_3$ is a hydrogen atom or a linear or branched $C_1$-$C_{20}$ alkyl radical. Preferably, X denotes a nitrogen atom or a $CR_3$ group where $R_3$ is a hydrogen atom or a linear or branched $C_1$-$C_6$ alkyl radical, for example an ethyl radical. More preferably still, X denotes a nitrogen atom.

According to one embodiment of the invention, $R_1$ and $R_1'$ are identical. Use of such a monomer during a polycondensation reaction with another at least difunctional monomer promotes a symmetry (isotropy and regularity) of the polymer chains synthesized.

According to one embodiment of the invention, $R_1$ and $R_1'$ respectively denote a —(CH($R_4$)—CH($R_5$)—O)$_n$— and —(CH($R_4$)—CH($R_5$)—O)$_m$— chain where n and m denote identical or different integral indices respectively ranging from 1 to 20, preferably from 3 to 20 and more preferably from 3 to 10 and $R_4$ and $R_5$ are independently chosen from a hydrogen atom, a linear or branched $C_1$-$C_6$ alkyl radical or an aryl radical. Preferably, $R_4$ and $R_5$ are independently chosen from a hydrogen atom, a linear or branched $C_1$-$C_3$ alkyl radical or a phenyl radical. More preferably still, $R_1$ denotes a —(CH$_2$—CH$_2$—O)$_n$—, —(CH(CH$_3$)—CH$_2$—O)$_n$—, —(CH$_2$—CH(CH$_3$)—O)$_n$—, —(CH$_2$—CH(CH$_2$—CH$_3$)—O)$_n$, —(CH(CH$_2$—CH$_3$)—CH$_2$—O)$_n$, —(CH(Ph)—CH$_2$—O)$_n$— or —(CH$_2$—CH(Ph)—O)$_n$— chain and $R_1'$ denotes a —(CH$_2$—CH$_2$—O)$_m$—, —(CH(CH$_3$)—CH$_2$—O)$_m$—, —(CH$_2$—CH(CH$_3$)—O)$_m$—, —(CH$_2$—CH(CH$_2$—CH$_3$)—O)$_m$, —(CH(CH$_2$—CH$_3$)—CH$_2$—O)$_m$, —(CH(Ph)—CH$_2$—O)$_m$— or —(CH$_2$—CH(Ph)—O)$_m$— chain, where Ph is a phenyl radical.

According to one embodiment of the invention, $R_1$ and $R_1'$ respectively denote a —(C=O)—O—(CH$_2$)$_2$— chain.

According to one embodiment of the invention, the monomer (A) is chosen from those in which:
X=N, $R_2$=—(CH$_2$)$_2$— and B=B2 with Z=O; or
X=N, $R_2$=—(CH$_2$)$_2$—NH—(CH$_2$)$_2$— and B=B2 with Z=O; or
X=N, $R_2$=—(CH$_2$—CH$_2$—NH)$_2$—(CH$_2$)$_2$— and B=B2 with Z=O; or
X=CH, $R_2$=—O—(CH$_2$)$_2$— and B=B2 with Z=O; or
X=N, $R_2$=—(CH$_2$)$_6$— and B=B4 with R=CH$_3$; or
X=N, $R_2$ is a single covalent bond and B=B1; or
X=N, $R_2$=—(CH$_2$)$_2$—NH—(C=O)—CH=CH—(C=O)— and B=B2 with Z=O; or
X=CR$_3$ with $R_3$ as defined above, $R_2$=—(CH$_2$)$_2$—NH—(C=O)—CH=CH—(C=O)—NH— and B=B2 with Z=O; or
X=CR$_3$ with $R_3$ as defined above, $R_2$=—(CH$_2$)$_2$—NH—CH$_2$— and B=B2 with Z=O; or
X=CR$_3$ with $R_3$ as defined above, $R_2$=—(CH$_2$)$_2$—O—CH$_2$— and B=B2 with Z=O; or
is a mixture of these compounds.

According to a more specific embodiment of the invention, the monomer (A) is chosen from those in which:
X=N, $R_2$=—(CH$_2$)$_2$— and B=B2 with Z=O; or
X=N, $R_2$=—(CH$_2$)$_2$—NH—(CH$_2$)$_2$— and B=B2 with Z=O; or
X=N, $R_2$=—(CH$_2$—CH$_2$—NH)$_2$—(CH$_2$)$_2$— and B=B2 with Z=O; or
X=CH, $R_2$=—O—(CH$_2$)$_2$— and B=B2 with Z=O; or
X=N, $R_2$=—(CH$_2$)$_6$— and B=B4 with R=CH$_3$; or
X=N, $R_2$ is a single covalent bond and B=B1; or
X=N, $R_2$=—(CH$_2$)$_2$—NH—(C=O)—CH=CH—(C=O)—, and B=B2 with Z=O; or
X=CR$_3$ with $R_3$ as defined above, $R_2$=—(CH$_2$)$_2$—NH—(C=O)—CH=CH—(C=O)—NH— and B=B2 with Z=O; or
X=CR$_3$ with $R_3$ as defined above, $R_2$=—(CH$_2$)$_2$—NH—CH$_2$— and B=B2 with Z=O; or
is a mixture of these compounds.

The monomer (A) is preferably chosen from those in which the associative group (B) is the (B2) group. More preferably still, the monomer (A) is chosen from those in which X=N, $R_2$=—(CH$_2$)$_2$— and B=B2 with Z=O.

Mention may more particularly be made, as examples of monomers (A) which can be employed according to the invention, of those corresponding to one of the following formulae:
X=N, $R_2$=—(CH$_2$)$_2$—, B=B2 with Z=O, $R_1$=$R_1'$=—(C=O)—O—(CH$_2$)$_2$— and $X_1$=$X_1'$=OH;
X=N, $R_2$=—(CH$_2$)$_2$—NH—(C=O)—CH=CH—(C=O)—, B=B2 with Z=O, $R_1$=$R_1'$=—(CH$_2$)$_2$— and $X_1$=$X_1'$=OH;
X=CR$_3$ with $R_3$ an ethyl radical, $R_2$=—(CH$_2$)$_2$—NH—(C=O)—CH=CH—(C=O)—NH—, B=B2 with Z=O, $R_1$=$R_1'$=—CH$_2$— and $X_1$=$X_1'$=OH;
X=N, $R_2$=—(CH$_2$)$_2$—, B=B2 with Z=O, $R_1$=$R_1'$=—(CH$_2$)$_2$— and $X_1$=$X_1'$=OH;
X=N, $R_2$=—(CH$_2$)$_2$—, B=B2 with Z=O, $R_1$=$R_1'$=—(CH$_2$)$_2$— and $X_1$=$X_1'$=COOH;
X=CR$_3$ with $R_3$ a hydrogen atom, $R_2$=—(CH$_2$)$_2$—NH—CH$_2$—, B=B2 with Z=O, $R_1$ a single bond, $R_1'$=—CH$_2$— and $X_1$=$X_1'$=COOH;
X=N, $R_2$=—(CH$_2$)$_2$—, B=B2 with Z=O, $R_1$=$R_1'$=—CH$_2$— and $X_1$=$X_1'$=COOH;
X=N, $R_2$=—(CH$_2$)$_2$—, B=B2 with Z=O, $R_1$=$R_1'$=—(CH$_2$)$_2$— and $X_1$=$X_1'$=CN;
X=N, $R_2$=—(CH$_2$)$_2$—, B=B2 with Z=O, $R_1$=$R_1'$=—(CH$_2$)$_3$— and $X_1$=$X_1'$=NH$_2$;
X=N, $R_2$=—(CH$_2$)$_2$—, B=B2 with Z=O, $R_1$=$R_1'$=—(CH$_2$)$_2$— and $X_1$=$X_1'$=CHO;
X=N, $R_2$=—(CH$_2$)$_2$—, B=B2 with Z=O, $R_1$=$R_1'$=—(CH$_2$)$_3$— and $X_1$=$X_1'$=OH;
X=CH, $R_2$=—(CH$_2$)$_2$—NH—CH$_2$—, B=B2 with Z=O, $R_1$ a single bond, $R_1'$=—(CH$_2$)$_2$— and $X_1$=$X_1'$=CN;
X=CH, $R_2$=—(CH$_2$)$_2$—NH—CH$_2$—, B=B2 with Z=O, $R_1$=—CH$_2$—, $R_1'$=—(CH$_2$)$_3$— and $X_1$=$X_1'$=NH$_2$;
X=CH, $R_2$=—(CH$_2$)$_2$—O—CH$_2$—, B=B2 with Z=O, $R_1$ a single bond, $R_1'$=—(CH$_2$)$_2$— and $X_1$=$X_1'$=CN;
X=CH, $R_2$=—(CH$_2$)$_2$—O—CH$_2$—, B=B2 with Z=O, $R_1$=—CH$_2$—, $R_1'$=—(CH$_2$)$_3$— and $X_1$=$X_1'$=NH$_2$;
or a mixture of these compounds.

Process for the Manufacture of the Monomer (A)

The monomer (A) is either commercially available or can be easily prepared by a procedure known to the person skilled in the art or by adapting a procedure available in the literature derived from patents, scientific publications, Chemical Abstracts and the Internet.

Mention may be made in these terms, of the document DE 3214909 and particularly the synthetic process described in Example 2 and also the document U.S. Pat. No. 2,858,319 and more particularly the synthetic process of example 1.

The monomer (A) can advantageously be obtained by reaction of an associative molecule corresponding to the formula (Ia):

$$\text{Ta—X—Ta}' \atop {|\atop R_2 \atop |\atop B}} \tag{Ia}$$

with at least one functionalization agent corresponding to one of the formulae (Ib), (Ib') and (Ic):

$X_1$—$R_1$—Tb　　(Ib)

$X_1'$—$R_1'$—Tb'　　(Ib')

$X_1$—$R_1$—Tc—$R_1'$—$X_1'$　　(Ic)

in which:

X, $R_2$, B, $X_1$, $X_1'$, $R_1$ and $R_1'$ are as defined above, Ta, Ta', Tb, Tb' and Tc are atoms or groups such that Ta is capable of reacting with Tb to form a covalent bond between X and $R_1$, Ta' is capable of reacting with Tb' to form a covalent bond between X and $R_1'$ and/or Ta and Ta' are capable of reacting with Tc to form the $R_1$—X($R_2$)—$R_1'$ group.

Ta, Ta', Tb, Tb' and Tc can in particular be reactive functional groups of any nature known to a person skilled in the art and can more particularly be independently chosen from the following functional groups: —$NH_2$, —COOH, —$PO_3H$, —$OPO_3H$, —OH, —SH, —COSH, —CSSH, —CSOH, -halogen, —CN, —NCO, —NCS, -epoxy, mesylate or tosylate.

According to one embodiment of the invention, Ta and Ta' are chosen from the amine, alcohol, carboxylic acid, mesylate, tosylate and halogen, in particular Cl, functional groups.

Associative Molecule of Formula (Ia)

According to one embodiment of the invention, the associative molecule is chosen from: 1-(2-aminoethyl)imidazolidin-2-one (UDETA), 1-(2-hydroxyethyl)imidazolidone (HEIO), 1-(2-[(2-aminoethyl)amino]ethyl)imidazolidone (UTETA), 1-(2-[2-{2-aminoethylamino}ethylamino]ethyl) imidazolidone (UTEPA), N-(6-aminohexyl)-N'-(6-methyl-4-oxo-1,4-dihydropyrimidin-2-yl)urea (UPy), 3-amino-1,2, 4-triazole (3-ATA) or of their mixtures.

More preferably, the associative molecule is UDETA.

The associative molecules UDETA, UTETA and UTEPA can be obtained by reaction of urea with a polyamine. For example, UDETA, UTETA and UTEPA can respectively be prepared by reacting urea with diethylenetriamine (DETA), triethylenetetramine (TETA) and tetraethylenepentamine (TEPA). The associative molecule HEIO can be obtained by reaction of urea with the corresponding diaminoalcohol, namely 2-[(2-aminoethypamino]ethanol.

Functionalization Agent

The choice of the functionalization agent depends on the nature of the reactive functional groups $X_1$ and $X_1'$ which it is desired to obtain in the monomer (A).

If it is desired for $X_1$ and/or $X_1'$ to be (an) alcohol functional group(s), for example, the functionalization agent can advantageously be chosen from:

epoxides and their mixtures, in particular ethylene oxide (EO), butylene oxide (BO), propylene oxide (PO), styrene oxide (SO) or their mixtures;

carbonates and their mixtures, in particular ethylene carbonate, propylene carbonate, glycerol carbonate or their mixtures;

aminoalcohols and their mixtures, in particular those of formula HO—$R_1$—NH—$R_1'$—OH, in which $R_1$ and $R_1'$ are as defined above, and those of formula $CH_3$—$CH_2$—C[($CH_2$—OH)$_2$]$NH_2$ and their mixtures.

If it is desired for $X_1$ and/or $X_1'$ to be (an) acid functional group(s), for example, the functionalization agent can advantageously be chosen from:

acrylic acid;
methacrylic acid;
itaconic acid;
monochloroacetic acid, monobromoacetic acid and their salts;
and their mixtures.

If it is desired for $X_1$ and/or $X_1'$ to be (a) nitrile functional group(s), for example, the functionalization agent can advantageously be chosen from:

acrylonitrile;
methyleneglutaronitrile;
their mixtures.

The nitriles obtained can advantageously be converted into amines according to any method known to a person skilled in the art, for example by hydrogenation.

If it is desired for $X_1$ and/or $X_1'$ to be (an) aldehyde functional group(s), for example, the functionalization agent can advantageously be acrolein.

The aldehydes obtained can advantageously be converted into amines according to any method known to a person skilled in the art, for example by reductive amination.

When an amination stage is carried out, the latter can be simultaneous with or consecutive to the hydrogenation stage.

The aldehydes obtained can also be converted into diols according to any method known to a person skilled in the art, for example by hydrogenation.

Polycondensate and its Process of Manufacture

Another subject matter of the invention is a process for the manufacture of a polycondensate employing at least one monomer (A) as defined above.

More particularly, this process comprises the following stages:

a) providing at least one monomer (A) as defined above,
b) optionally providing at least one at least monofunctional, advantageously at least difunctional, indeed even trifunctional or more, monomer (C) different from the monomer (A) and not comprising an associative group,
c) carrying out a polymerization reaction by polycondensation of the monomer (A) and optionally of the monomer (C),
d) obtaining a polycondensate.

The process according to the invention thus makes it possible to obtain a supramolecular polycondensate carrying pendant associative groups in the polymer chain by a simple polycondensation reaction.

The polycondensation reaction can be carried out according to any technique known to a person skilled in the art or by adapting (temperature, pressure, and the like) a procedure available in the literature derived from patents, scientific publications, Chemical Abstracts and the Internet.

The term "at least one monomer (A)" denotes the nature and not the number of moles of monomers (A) employed. Use may thus be made of a monomer (A) which corresponds to a single formula (I) or several monomers (A) of different formulae (I).

Respectively, the term "at least one monomer (C)" denotes the nature and not the number of moles of monomers (C) employed. Use may thus be made of a monomer (C) which corresponds to a single chemical formula or several monomers (C) of different chemical formulae.

The term "polycondensation of the monomer (A) and of the monomer (C)" is understood to mean the formation of a polycondensate incorporating units resulting from the monomers (A) and (C).

The term "obtaining a polycondensate" in stage d) is understood to mean the polycondensate incorporating units resulting from the monomers (A) and optionally (C) which is obtained directly at the end of stage c) or optionally after one or more intermediate stages, for example of extraction and/or of purification.

By virtue of the monomers carrying associative groups of the invention, the process for the synthesis of polymers according to the invention makes it possible to readily vary the number and/or the position of the associative groups incorporated in the chains of the polymer synthesized. It is sufficient, for example, to adjust the ratio of monomer (A) with regard to the total number of monomers employed in order to modify the number of associative groups in the polymer obtained. The position of the associative groups can, for its part, be modified by introducing, for example, the monomers (A) and the optional monomers (C) in sequential manner. It is thus possible to synthesize copolymers comprising blocks carrying associative groups.

According to one embodiment of the invention, the process for the manufacture of the polycondensate employs at least one first monomer (A) and one second monomer (A) of different formulae (I), the reactive functional groups $X_1$ and $X_1'$ of the first monomer (A) being different from the reactive functional groups $X_1$ and $X_1'$ of the second monomer (A) and being capable of reacting with the reactive functional groups $X_1$ and $X_1'$ of the second monomer (A). It is understood that the process for the manufacture of the polycondensate can in addition employ one or more other identical or different monomers (A) of formula (I), insofar as their reactive functional groups are capable of reacting with the reactive functional groups of at least one of the monomers (A) already present. The monomers (A) can be introduced simultaneously or sequentially.

According to one embodiment of the invention, the reactive functional groups of the first monomer (A) are amine functional groups and the reactive functional groups of the second monomer (A) are acid functional groups, so that the polycondensate formed is a polyimide.

According to one embodiment of the invention, the reactive functional groups of the first monomer (A) are isocyanate functional groups and the reactive functional groups of the second monomer (A) are alcohol functional groups, so that the polycondensate formed is a polyurethane.

According to one embodiment of the invention, the reactive functional groups of the first monomer (A) are isocyanate functional groups and the reactive functional groups of the second monomer (A) are amine functional groups, so that the polycondensate formed is a polyurea.

According to one embodiment of the invention, the reactive functional groups of the first monomer (A) are acid functional groups and the reactive functional groups of the second monomer (A) are alcohol functional groups, so that the polycondensate formed is a polyester.

According to another embodiment of the invention, the process for the manufacture of the polycondensate employing at least one monomer (A) of formula (I), the reactive functional groups $X_1$ and $X_1'$ of which are different and capable of reacting with one another.

For example, according to one embodiment of the invention, the process for the manufacture of the polycondensate employs a monomer (A), the functional group $X_1$ of which is an amine functional group and the functional group $X_1'$ of which is an acid functional group, so that the polycondensate formed is a polyamide.

According to one embodiment of the invention, the process for the manufacture of the polycondensate employs a monomer (A), the functional group $X_1$ of which is an isocyanate functional group and the $X_1'$ functional group of which is an alcohol functional group, so that the polycondensate formed is a polyurethane.

According to one embodiment of the invention, the process for the manufacture of the polycondensate employs a monomer (A), the functional group $X_1$ of which is an isocyanate functional group and the $X_1'$ functional group of which is an amine functional group, so that the polycondensate formed is a polyurea.

According to one embodiment of the invention, the isocyanate functional groups can be employed in the blocked form, according to the methods known to a person skilled in the art.

According to one embodiment of the invention, the process for the manufacture of the polycondensate employs a monomer (A), the $X_1$ functional group of which is an acid functional group and the $X_1'$ functional group of which is an alcohol functional group, so that the polycondensate formed is a polyester.

According to another embodiment of the invention, the process for the manufacture of the polycondensate employs, in addition to the monomer (A) or the identical or different monomers (A) of formulae (I), an at least monofunctional, difunctional, indeed even trifunctional or more, monomer (C) different from the monomer (A) which does not comprise an associative group and which is chosen from the monomers known to a person skilled in the art for the synthesis of polycondensates.

According to a more specific embodiment of the invention, the monomer (C) is a difunctional monomer corresponding to the formula (II):

$$[Y_1—R_5—Y_1'] \quad (II)$$

in which:

$Y_1$ and $Y_1'$ denote identical or different functional groups (known as "reactive functional groups") independently chosen from —$NH_2$, —COOH, —$PO_3H$, —$OPO_3H$, —OH, —SH, —COSH, —CSSH, —CSOH, -halogen, —CN, —NCO, —NCS or -epoxy, and $R_5$ denotes a saturated or unsaturated and linear or branched $C_1$-$C_{30}$ hydrocarbon chain which is optionally interrupted by one or more heteroatoms chosen from nitrogen, oxygen, sulfur, silicon and phosphorus or by a saturated, partially unsaturated or completely unsaturated ring optionally comprising one or more heteroatoms chosen from nitrogen, oxygen, sulfur, silicon and phosphorus.

According to an embodiment, $Y_1$ and $Y_1'$ denote reactive functional groups independently chosen from —$NH_2$, —COOH, —OH and —NCO.

According to one embodiment, $Y_1$ and $Y_1'$ denote different reactive functional groups. This makes it possible, for example, to react the monomer (C) with several types of monomers (A) during the same reaction or with a monomer (A) carrying different reactive functional groups $X_1$ and $X_1'$.

Mention may be made, as nonlimiting examples of difunctional monomers (C) corresponding to the above formula (II), of those already mentioned above and in particular:

aromatic diacids, such as iso- and terephthalic acids, 2,6-, 1,5- or 2,7-naphthalenedicarboxylic acids, 4,4'-dicarboxydiphenyl ether, 4,4'-dicarboxybiphenyl or furandicarboxylic acid, aliphatic diacids, for example linear or branched $C_4$ to $C_{24}$ aliphatic diacids, such as adipic acid, sebacic acid, dodecane-1,12-dioic acid, suberic acid, azelaic acid, undecanedioic acid, dodecanedioic acid, tetradecanedioic acid, pentadecanedioic acid, thapsic (hexadecanedioic acid) or octadecanedioic acid, cycloaliphatic diacids, such as cyclohexane-1,4-dicarboxylic acid, cyclohexane-1,3-dicarboxylic acid or cyclobutane-1,3-dicarboxylic acid, phthalic acid, isophthalic acid, trimellitic acid or terephthalic acid, cycloaliphatic diamines, for example bis(3,3'-methyl-4,4'-aminocyclohexyl)-methane, bis(4,4'-aminocyclohexyl) methane, isophoronediamine, bis(3,5-dialkyl-4-aminocyclohexyl)methane, bis(3,5-dialkyl-4-aminocyclohexyl)ethane, bis(3,5-dialkyl-4-aminocyclohexyl)propane, 2,2-bis(3-methyl-4-aminocyclohexyl)propane (BMACP), isopropylidenedi(cyclohexylamine) (PACP) or 2,6-bis(aminomethyl) norbornane (BAMN), aliphatic diamines, for example linear or branched $C_2$ to $C_{24}$ aliphatic diamines, such as 1,6-hexamethylènediamine, 1,19-nonamethylenediamine, 1,10-deca-methylenediamine or 1,12-dodecamethylenediamine, aliphatic diols, preferably comprising at least 6 carbon atoms, such as hexanediols, heptanediols, octanediols, nonanediols, decanediols, undecanediols or dodecanediols (typically 1,6-hexanediol, 1,7-heptanediol, 1,8-octanediol, 1,9-nonane-diol, 1,10-decanediol, 1,11-undecanediol or 1,12-dodecanediol), aromatic diols, such as resorcinol, hydroquinone or bisphenol A, branched diols, such as 1,6-hexylene glycol, aliphatic or cycloaliphatic diisocyanates, such as 1,6-hexamethylene diisocyanate, 4,4'-dicyclohexylmethane diisocyanate, 1,4-cyclohexane diisocyanate, bis (isocyanatomethyl)cyclohexane or isophorone diisocyanate, aromatic diisocyanates, such as 2,4-toluene diisocyanate, 2,6-toluene diisocyanate, 4,4'-methylenediphenyl diisocyanate, 2,4'-methylenediphenyl diisocyanate, paraphenyl diisocyanate, 1,5-naphthalene diisocyanate or IPDI (isophorone diisocyanate), amino acids, for example $C_5$ to $C_{14}$ amino acids, such as 11-aminoundecanoic acid or 10-aminodecanoic acid.

The content of monomer (C) represents the remainder to 100 mol % of the content of monomer (A) employed, with regard to the total number of moles of monomers used to manufacture the polycondensate.

Another subject matter of the invention is the polycondensate capable of being obtained by the manufacturing process described in detail above.

According to one embodiment of the invention, the polycondensate comprises from 0.1 mol % to 50 mol %, preferably from 1 mol % to 20 mol %, of associative groups B, with regard to the total number of moles of polycondensate.

The number of associative groups B present in the polycondensate can easily be adjusted by varying the ratio of the number of moles of monomers (A) to the total number of moles of monomers (A) and optionally (C) used.

According to one embodiment of the invention, the polycondensate is a homopolymer, a block copolymer or a random copolymer.

Applications

Another subject matter of the invention is the use of a monomer or of a polycondensate according to the invention to manufacture an article or a composition.

Finally, a subject matter of the invention is such an article and such a composition.

The term "article" is understood to mean a part having two dimensions, for example a sheet, or a part having three dimensions.

The term "composition" is understood to mean a liquid solution or dispersion, in water and/or in one or more solvents, at ambient temperature.

The monomers and polycondensates according to the invention can be used in numerous fields, for example aeronautics, the space sector, the motor vehicle industry, the naval industry, energy, the railroad industry, wind power, photovoltaics, sports and leisure, including water sports, the construction industry, civil engineering, the paper industry and the textile industry, and generally in any field where high stresses, in particular mechanical and/or thermal stresses, are encountered.

Mention may in particular be made, as articles, of profiled reinforcements, hulls, such as a boat hull, or panels.

Preference is given, as compositions, to adhesive compositions, such as an adhesive mass, an adhesive emulsion, an organic or aqueous adhesive solution or also a binder, such as binder for paint, ink, varnish and/or textile protection.

The term "adhesive mass" is understood to mean a formulated or nonformulated polycondensate but devoid of solvent, that is to say an adhesive composition which does not require evaporation in order to establish adhesiveness.

A better understanding of the invention will be obtained in the light of the following examples, given for purposes of illustration only and which do not have the aim of restricting the scope of the invention, defined by the appended claims.

EXAMPLES

Synthesis of Monomers (A)

Example 1A

Preparation of a diol Carrying Associative Groups: 1-[2-[bis(2hydroxyethyl)amino]ethyl]-2-imidazolidinone 500 g (3.87 M) of N-(2-aminoethyl)imidazolidin-2-one and 0.2% by weight of 50% hypophosphorous acid in water (catalyst) are charged to a 6 l autoclave cleaned and dried beforehand and equipped in order to carry out an alkoxylation. The minimum heel is 500 g, in order to ensure good stirring of the reaction medium. The characteristics of the amine are determined by a measurement in its total alkalinity (7.6 meq/g) and of its water content (500 ppm). The water content is important in order to limit the formation of impurities. The autoclave is closed and purges of the air from the gas phase are carried out by 3 slow compressions/decompressions with nitrogen. During the final purge, the leaktightness of the assembly is tested by applying a pressure greater by 20% than that of the pressure used in the test, at a temperature of 60° C. The medium is brought to a temperature ranging from 80° C. to 90° C. and the nitrogen pressure is adjusted to 2.2 bar absolute. The ethoxylation of the amine is started by introducing ethylene oxide (EO) so as not to exceed an overall pressure of 3.5 bar. The initiating of the reaction is reflected by an exothermicity. In total, 340 g (7.73 M) of EO are introduced at a flow rate which depends on the exothermicity of the reaction and while maintaining a pressure in the vicinity of 3.5 bar. When all the EO is introduced, reaction is allowed to take place until the pressure is stable and in the vicinity of the residual pressure of the nitrogen. The reaction medium is cooled to 60° C. The assembly is subsequently purged with nitrogen and the product is degassed, so as to remove the residual traces of EO therefrom. After emptying, 830 g of a pale-yellow viscous liquid product are obtained. An NMR analysis is carried out on a Bruker AV 500 spectrometer equipped with a 5 mm TXI ($^1$H/$^{13}$C/$^{31}$P) probe. The sample is dissolved in titrated chloroform and examined in $^{13}$C. This analysis shows that 1[2-[bis(2-hydroxyethyl)amino]ethyl]-2-imidazolidinone is concerned.

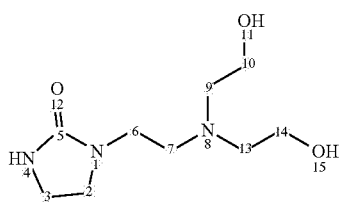

| Atom number | $^{13}$C Chemical shift |
| --- | --- |
| 2 | 163.7 |
| 3 | 38.07 |
| 5 | 45.04 |
| 6 | 42.35 |
| 7 | 53.08 |
| 9, 13 | 57.20 |
| 10, 14 | 59.57 |

Example 1B

Preparation of a diol Carrying Associative Groups, 1-(2-[bis(2-hydroxy-propyl)amino]ethyl)imidazolidin-2-one Example 1A is repeated, ethylene oxide being replaced with propylene oxide.

Example 1C

Preparation of a diol Carrying Associative Groups: 1-(2-[bis(2-hydroxy-butyl)amino]ethyl)imidazolidin-2-one Example 1A is repeated, ethylene oxide being replaced with butylene oxide.

Example 1D

Preparation of a diol Carrying Associative Groups: 1-(2-[bis(2-hydroxy-styryl)amino]ethyl)imidazolidin-2-one Example 1A is repeated, ethylene oxide being replaced with styrene oxide.

Example 1E

Preparation of a diol Carrying Associative Groups: polyethoxylated, -propoxylated and -butoxylated N-(2-aminoethyl)imidazolidin-2-one Example 1A is repeated, ethylene oxide being replaced with a mixture of ethylene oxide, propylene oxide and butylene oxide: in a first test 1 Ea, the various oxides are introduced simultaneously, as a mixture; in a second test 1 Eb, the various oxides are introduced sequentially,

Example 2A

Preparation of a diacid Carrying Associative Groups: 3,3'-{[2-(2-oxoimidazolidin-1-yl)ethyl]imino}dipropanoic acid

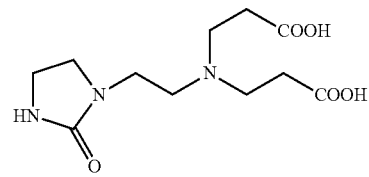 [SMILES: O=C(O)CCN(CCC(=O)O)CCN1CCNC1=O]

200 g of isopropanol and 28.8 g (0.2 M) of N-(2-aminoethyl)imidazolidin-2-one with a purity of 95% are charged to a 500 cm$^3$ reactor equipped with a mechanical stirrer, with heating, with a dropping funnel and with a system for rendering inert with nitrogen. The medium is brought to 60° C. and then 36 g (0.5 M) of glacial acrylic acid are run in slowing. The mixture is maintained at 60° C. for 2 hours. The mixture is cooled and a beige powder is recovered by filtration which weighs 40.8 g after drying. The isolated yield is 75%. The melting point, measured by DSC, is 159-160° C. An NMR analysis shows that it is 3,3'-{[2-(2-oxoimidazolidin-1-yl)ethyl]imino}dipropanoic acid.

Example 2B

Preparation of a diacid Carrying Associative Groups: [2-(2-oxo-1-imidazolidinyl)ethylimino]diacetic acid

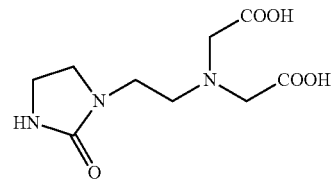 [SMILES: O=C(O)CN(CCN1CCNC1=O)CC(=O)O]

233 g (2 M) of sodium monochloroacetate, 500 g of water and 171 g (1 M) of barium hydroxide are charged to a 2000 cm$^3$ reactor equipped with a mechanical stirrer, heating, a dropping funnel and a system for rendering inert with nitrogen. The solution is maintained at 0° C. 129 g (1 M) of N-(2-aminoethyl)imidazolidin-2-one in 300 g of water are run in dropwise. After maintaining at ambient temperature for 3 hours, 201 g of the barium disalt (barium salt of [2-(2-oxo-1-imidazolidinyl)ethylimino]diacetic acid) are recovered by filtration. The product is resuspended in water and acidified with 98% sulfuric acid. If required, methanol is added to promote the precipitation. 55 g of [2-(2-oxo-1-imidazolidinyl)ethylimino]diacetic acid are thus collected, exhibiting a melting point between 194° C. and 196° C., measured on a Kofler bench.

Example 2C

Preparation of a diacid Carrying Associative Groups: [2-(2-oxo-1-imidazolidinyl)ethylimino]diacetic acid

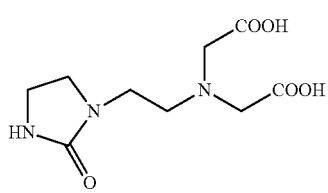

Example 2B is repeated, sodium monochloroacetate being replaced with sodium monobromoacatate.

Example 3

Preparation of a dinitrile Carrying Associative Groups: 1-[2-[bis(2-cyanoethyl)amino]ethyl]-2-imidazolidinone

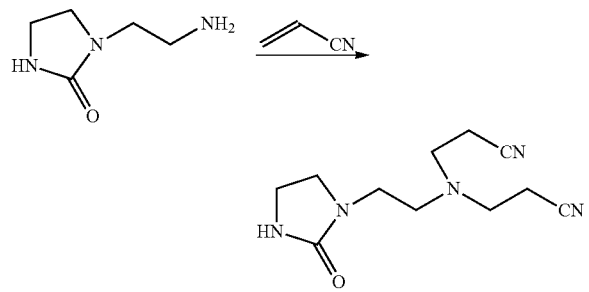

129 g (1 M) of N-(2-aminoethyl)imidazolidin-2-one and 2 g of water are charged to a 500 cm³ autoclave equipped with a magnetic stirrer with self-suction turbine, a jacket for heating and a system for rendering the reactor headspace inert with nitrogen. The headspace of the reactor is rendered inert with nitrogen and then the product is brought to 80° C. 58 g (1.1 M) of acrylonitrile are introduced over 30 min by means of a pump and the mixture is subsequently kept stirred for 1 H. For the 2nd phase of the reaction, 4.4 g (0.048 M) of oxalic acid dissolved in 9 g of water are introduced. The autoclave is purged with nitrogen and then the temperature is brought to 130° C. before again introducing, via the pump, 58 g (1 M) of acrylonitrile in 30 min. The reaction is continued until the primary amine is very predominantly in a tertiary amine form. Subsequently, the mixture is cooled to 90° C. and a stripping of nitrogen is carried out in order to remove the water and the excess of acrylonitrile. The expected product is obtained with a yield of 95%. The crude reaction product can be used as it is.

Example 4

Preparation of a triamine Carrying Associative Groups: 1-[2-[bis(3-aminopropyl)amino]ethyl]-2-imidazolidinone and the Corresponding diisocyanate 117.5 g (0.5 M) of 1-[2-[bis(2-cyanoethyl)amino]ethyl]-2-imidazolidinone with 120 g of ethanol and 9 g of Raney nickel catalyst are charged to a 500 cm³ autoclave equipped with a magnetic stirrer with self-suction turbine, a jacket for heating and a system for rendering the reactor headspace inert with nitrogen. The headspace of the reactor is rendered inert with nitrogen. The leaktightness of the autoclave is confirmed and then 17 g (1 M) of ammonia are introduced at ambient temperature. The reaction medium is brought to 50° C. The hydrogen is subsequently introduced while gradually bringing the temperature to 80° C. and at a total pressure of 150 bar. Hydrogenation is continued under these conditions until no hydrogen is being consumed. The reaction medium is cooled to 50° C., degassed and purged with nitrogen. The catalyst is filtered off and then the solvent is evaporated. The triamine is obtained with a yield of 80%. Purification is carried out by short-path scraped film distillation.

A phosgenation, by introducing COCl₂, carried out under conventional conditions makes it possible to convert the terminal amine functional groups of the monomer synthesized in the isocyanate functional groups.

Example 5

Preparation of a dinitrile Carrying Associative Groups and of a triamine Carrying Associative Groups

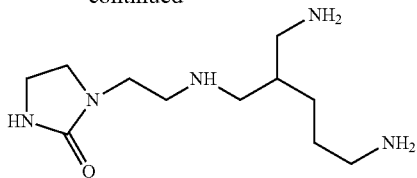

129 g (1 M) of N-(2-aminoethyl)imidazolidin-2-one and 2 g of water are charged to a 500 cm³ reactor equipped with a mechanical stirrer, a jacket for heating, a dropping funnel and a system for rendering inert with nitrogen. The product is brought to 75-80° C. and then 116 g (1.1 M) of methyleneglutaronitrile are run in slowly. Reaction is allowed to take place, the reaction being monitored by potentiometric titration of the primary amines to given secondary amines. At the end of the reaction, the dinitrile is obtained with a yield of 89%. The product can be used as is.

117.5 g (0.5 M) of the condensation product of N-(2-aminoethyl)imidazolidin-2-one with methyleneglutaronitrile (MGN) obtained, with 100 g of ethanol and 9 g of Raney nickel catalyst, are charged to a 500 cm³ autoclave equipped with a magnetic stirrer with a self-suction turbine, a jacket for heating and a system for rendering the reactor headspace inert with nitrogen. The headspace of the reactor is rendered inert with nitrogen. The leaktightness of the autoclave is confirmed and then 17 g (1 M) of ammonia are introduced at ambient temperature. The reaction medium is brought to 50° C. The hydrogen is subsequently introduced while gradually bringing the temperature to 100° C. and at a total pressure of 150 bar. Hydrogenation is continued under these conditions until consumption of hydrogen has ceased. The reaction medium is cooled to 50° C., degassed and purged with nitrogen. The catalyst is filtered off and then the solvent is evaporated. The triamine is obtained with a yield of 92%. Purification is carried out by short-path scraped film distillation.

Example 6

Preparation of a dinitrile Carrying Associative Groups and of an Ether Diamine Carrying Associative Groups

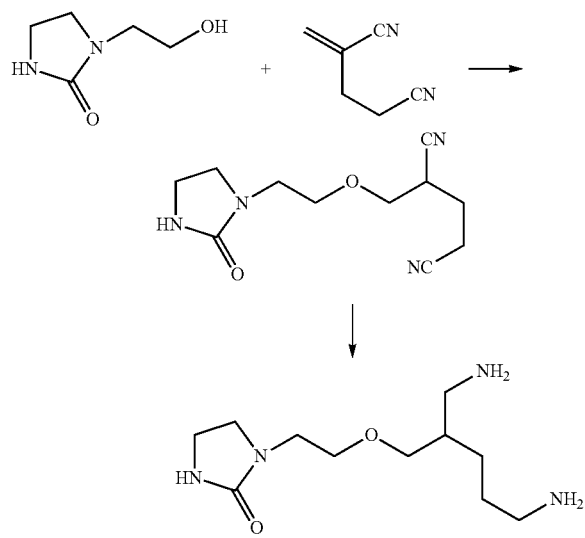

130 g (1 M) of N-(2-hydroxyethyl)imidazolidin-2-one and 2 g of potassium hydroxide pellets are charged to a 500 cm³ reactor equipped with a mechanical stirrer, a jacket for heating, a dropping funnel and a system for rendering inert with nitrogen. The product is brought to 80° C. and then 116 g (1.1 M) of methyleneglutaronitrile are run in slowly. At the end of the reaction, when there is virtually no more methyleneglutaronitrile, the catalyst is neutralized with an acid. The expected dinitrile is obtained with a yield of 95%. The product can be used as is or purified by distillation in order to separate it from the excess methyleneglutaronitrile.

118 g (0.5 M) of the condensation product of N-(2-hydroxyethyl)imidazolidin-2-one with methyleneglutaronitrile (MGN) obtained, with 100 g of ethanol and 9 g of Raney nickel catalyst, are charged to a 500 cm³ autoclave equipped with a magnetic stirrer with a self-suction turbine, a jacket for heating and a system for rendering the reactor headspace inert with nitrogen. The headspace of the reactor is rendered inert with nitrogen. The leaktightness of the autoclave is confirmed and then 17 g (1 M) of ammonia are introduced at ambient temperature. The reaction medium is brought to 50° C. The hydrogen is subsequently introduced while gradually bringing the temperature to 100° C. and at a total pressure of 150 bar. Hydrogenation is continued under these conditions until consumption of hydrogen has ceased. The reaction medium is cooled to 50° C., degassed and purged with nitrogen. The catalyst is filtered off and then the solvent is evaporated. The ether diamine is obtained with a yield of 90%. Purification is carried out by short-path scraped film distillation.

Synthesis of Polycondensates

Tests on the synthesis of polycondensates (polyesters) were carried out starting from the diol synthesized in example 1 (monomer (A)) with adipic acid (monomer (C)). The diol obtained in example 1 (monomer (A)) and the adipic acid (monomer (C)) are introduced in an equimolar amount, under nitrogen, into a 500 cm³ glass reactor equipped with an adjustable-speed stirrer motor, with inlets which make it possible to introduce reactants, inert gases, such as nitrogen, and measurement probes (for example, temperature probes), with a system for condensation/extraction of vapor which can be connected to a system for producing a vacuum (vacuum pump, vacuum trap, and the like) and with a jacket which makes possible the heating or cooling of the contents of the reactor by circulation of a heat-exchange fluid, for example the oil of a thermostatically controlled bath. The water generated is distilled and collected continuously via a Dean & Stark apparatus. The reaction is continued until the distillation of the water stops. The polyester obtained is extracted from the reactor in the molten state.

The invention claimed is:

1. A method of manufacturing a polycondensate, wherein the method comprises using an at least difunctional monomer (A) corresponding to the formula (I):

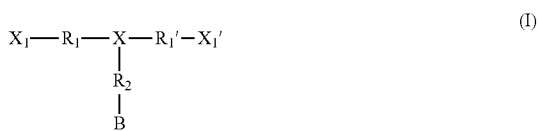

in which:
X₁ and X₁' denote identical or different functional groups independently chosen from —NH₂, —COOH, —OH, —CN, —NCO or -epoxy;

X denotes the nitrogen atom, or a CR₃ group where R₃ is chosen from the hydrogen atom or a linear or branched C₁-C₂₀ alkyl radical;

R₂ represents a saturated or unsaturated and linear or branched C₁-C₂₀ hydrocarbon chain which is optionally substituted by one or more =O, —OH or —NH₂ groups and optionally interrupted by one or more heteroatoms chosen from nitrogen, oxygen or silicon;

R₁ and R₁', which are identical or different, represent, independently of one another, a single bond or a saturated or unsaturated and linear or branched C₁-C₂₀ hydrocarbon chain which is optionally substituted and optionally interrupted by one or more heteroatoms chosen from nitrogen or oxygen or silicon;

B denotes an associative group represented by the formula (B2):

[structure: imidazolidine with N—CH₃, =Z, and NH]

in which:
Z represents an oxygen or sulfur atom.

2. The method as claimed in claim 1, wherein the monomer (A) is employed in a content ranging from 0.1 mol % to 100 mol % with regard to the total number of moles of monomers used to manufacture the polycondensate.

3. The method as claimed in claim 1, wherein X₁ and X₁' denote functional groups independently chosen from —NH₂, —COOH, —OH, —CN or —NCO.

4. The method as claimed in claim 1, wherein X₁ and X₁' denote different functional groups.

5. The method as claimed in claim 1, wherein X denotes a nitrogen atom or a CR₃ group with R₃ a hydrogen atom or a linear or branched C₁-C₆ alkyl radical.

6. The method as claimed in claim 1, wherein R₁ and R₁' are identical.

7. The method as claimed in claim 1, wherein R₁ and R₁' respectively denote a —(CH(R₄)—CH(R₅)—O)$_{n-1}$—CH(R₄)—CH(R₅)— and —(CH(R₄)—CH(R₅)—O)$_{m-1}$—CH(R₄)—CH(R₅)— chain where n and m denote identical or different integral indices ranging respectively from 1 to 20 and R₄ and R₅ are independently chosen from a hydrogen atom, a linear or branched C₁-C₆ alkyl radical or an aryl radical.

8. The method as claimed in claim 7, wherein R₁ denotes a —(CH₂—CH₂—O)$_{n-1}$—CH₂—CH₂—, —(CH(CH₃)—CH₂—O)$_{n-1}$—CH(CH₃)—CH₂—, —(CH₂—CH(CH₃)—O)$_{n-1}$—CH₂—CH(CH₃)—, —(CH₂—CH(CH₂—CH₃)—O)$_{n-1}$—CH₂—CH(CH₂—CH₃)—, —(CH(CH₂—CH₃)—CH₂—O)$_{n-1}$—CH(CH₂—CH₃)—CH₂—, —(CH(Ph)—CH₂—O)$_{n-1}$—CH(Ph)—CH₂— or —(CH₂—CH(Ph)—O)$_{n-1}$—CH₂—CH(Ph)— chain and R₁' denotes a —(CH₂—CH₂—O)$_{m-1}$—CH₂—CH₂—, —(CH(CH₃)—CH₂—O)$_{m-1}$—CH(CH₃)—CH₂—, —(CH₂—CH(CH₃)—O)$_{m-1}$—CH₂—CH(CH₃)—, —(CH₂—CH(CH₂—CH₃)—O)$_{m-1}$—CH₂—CH(CH₂—CH₃)—, —(CH(CH₂—CH₃)—CH₂—O)$_{m-1}$—CH(CH₂—CH₃)—CH₂—, —(CH(Ph)—CH₂—O)$_{m-1}$—CH(Ph)—CH₂— or —(CH₂—CH(Ph)—O)$_{m-1}$—CH₂—CH(Ph)— chain, where Ph is a phenyl radical.

9. The method as claimed in claim 1, wherein the monomer (A) is chosen from those in which Z=O and:
X=N, R₂=—(CH₂)₂—; or
X=N, R₂=—(CH₂)₂—NH—(CH₂)₂—; or
X=N, R₂=—(CH₂—CH₂—NH)₂—(CH₂)₂—; or
X=CH, R₂=—O—(CH₂)₂—; or
X=CR₃ with R₃ as defined above, R₂=—(CH₂)₂—NH—CH₂—; or
X=CR₃ with R₃ as defined above, R₂=—(CH₂)₂—O—CH₂—; or
is a mixture of these compounds.

10. The method as claimed in claim 1, wherein the monomer (A) is employed in a content of from 1 mol % to 80 mol % with regard to the total number of moles of monomers used to manufacture the polycondensate.

11. The method as claimed in claim 1, wherein the monomer (A) is employed in a content of from 1 mol % to 50 mol % with regard to the total number of moles of monomers used to manufacture the polycondensate.

12. The method as claimed in claim 1, wherein X₁ and X₁' denote different functional groups capable of reacting with one another.

13. The method as claimed in claim 1, wherein R₁ and R₁' respectively denote a —(CH(R₄)—CH(R₅)—O)$_{n-1}$—CH(R₄)—CH(R₅)—and —(CH(R₄)—CH(R₅)—O)$_{m-1}$—CH(R₄)—CH(R₅)— chain where n and m denote identical or different integral indices ranging respectively from 1 to 20 and R₄ and R₅ are independently chosen from a hydrogen atom, a linear or branched C₁-C₃ alkyl radical or a phenyl radical.

14. A process for manufacturing a polycondensate comprising the following stages:
a) providing at least one monomer (A);
b) optionally providing at least one at least monofunctional monomer (C) different from the monomer (A) and not comprising an associative group;
c) carrying out a polymerization reaction by polycondensation of the monomer (A) and optionally of the monomer (C); and
d) obtaining a polycondensate;
wherein monomer (A) corresponds to the formula (I):

$$X_1\!-\!R_1\!-\!X\!-\!R_1'\!-\!X_1' \quad \text{(I)}$$
$$\phantom{X_1\!-\!R_1\!-\!}\overset{|}{R_2}$$
$$\phantom{X_1\!-\!R_1\!-\!}\overset{|}{B}$$

in which:
X₁ and X₁' denote identical or different functional groups independently chosen from —NH₂, —COOH, —OH, —CN, —NCO or -epoxy;

X denotes the nitrogen atom, or a CR₃ group where R₃ is chosen from the hydrogen atom or a linear or branched C₁-C₂₀ alkyl radical;

R₂ represents a saturated or unsaturated and linear or branched C₁-C₂₀ hydrocarbon chain which is optionally substituted by one or more =O, —OH or —NH₂ groups and optionally interrupted by one or more heteroatoms chosen from nitrogen, oxygen or silicon;

R₁ and R₁', which are identical or different, represent, independently of one another, a single bond or a saturated or unsaturated and linear or branched $C_1$-$C_{20}$, hydrocarbon chain which is optionally substituted and optionally interrupted by one or more heteroatoms chosen from nitrogen or oxygen or silicon;

B denotes an associative group represented by the formula (B2):

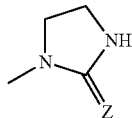

in which:

Z represents an oxygen or sulfur atom.

15. The process as claimed in claim 14, employing at least first and second monomers (A) of different formulae (I), the $X_1$ and $X_1'$ functional groups of the first monomer (A) being different from the $X_1$ and $X_1'$ functional groups of the second monomer (A) and being capable of reacting with the latter functional groups.

16. The process as claimed in claim 14, employing at least one monomer (A), the $X_1$ and $X_1'$ functional groups of which are different and capable of reacting with one another.

17. The process as claimed in claim 14, additionally employing at least one at least monofunctional monomer (C) different from the monomer (A) and not comprising an associative group.

18. The process as claimed in claim 14, additionally employing at least one difunctional monomer (C) corresponding to the formula (II):

$$[Y_1-R_5-Y_1'] \quad (II)$$

in which:

$Y_1$ and $Y_1'$ denote identical or different functional groups independently chosen from —$NH_2$, —COON, —OH, —CN, —NCO or -epoxy; and $R_5$ denotes a saturated or unsaturated and linear or branched $C_1$-$C_{30}$ hydrocarbon chain which is optionally interrupted by one or more heteroatoms chosen from nitrogen and oxygen, or by a saturated, partially unsaturated or completely unsaturated ring optionally comprising one or more heteroatoms chosen from nitrogen and oxygen.

19. A polycondensate carrying pendant associative group(s) obtained by the process as claimed in claim 14, comprising from 0.1 mol % to 50 mol % with regard to the total number of moles of polycondensate.

20. A method of manufacturing a polymer article or composition, comprising using the polycondensate of claim 19.

* * * * *